United States Patent
Ha (10) Patent No.: US 10,543,124 B2
(45) Date of Patent: Jan. 28, 2020

(54) CONTACT LENS AND OPHTHALMIC TREATMENT DEVICE HAVING SAME

(71) Applicant: Lutronic Vision Inc, Burlington, MA (US)

(72) Inventor: Tae Ho Ha, Gyeonggi-do (KR)

(73) Assignee: LUTRONIC VISION INC, Burlington, MA (US)

( * ) Notice: Subject to any disclaimer, the term of this patent is extended or adjusted under 35 U.S.C. 154(b) by 498 days.

(21) Appl. No.: 14/907,519

(22) PCT Filed: Jul. 21, 2014

(86) PCT No.: PCT/KR2014/006590
§ 371 (c)(1),
(2) Date: Jan. 25, 2016

(87) PCT Pub. No.: WO2015/012544
PCT Pub. Date: Jan. 29, 2015

(65) Prior Publication Data
US 2016/0158058 A1     Jun. 9, 2016

(30) Foreign Application Priority Data
Jul. 25, 2013 (KR) .................. 10-2013-0087976

(51) Int. Cl.
*A61F 9/009* (2006.01)
(52) U.S. Cl.
CPC .................... *A61F 9/009* (2013.01)

(58) Field of Classification Search
CPC ........................................ A61F 9/009
USPC ................................................ 606/4
See application file for complete search history.

(56) References Cited

U.S. PATENT DOCUMENTS

| 2006/0111697 | A1 | 5/2006 | Brinkmann et al. |
| 2008/0294153 | A1* | 11/2008 | Altshuler ........... A45D 26/0061 606/9 |
| 2010/0274228 | A1* | 10/2010 | Mrochen ............. A61F 9/009 604/541 |
| 2010/0324543 | A1* | 12/2010 | Kurtz .................. A61F 9/008 606/6 |

FOREIGN PATENT DOCUMENTS

| KR | 20130034924 A | 4/2013 |
| WO | 2006090217 A1 | 8/2006 |
| WO | 2012031277 A1 | 3/2012 |

* cited by examiner

Primary Examiner — Aaron F Roane (57) ABSTRACT

A contact lens, according to the present invention, comprises: a housing having a light-incident part on which a therapeutic beam oscillated from a beam generation part is incident, and a light-emitting part for guiding the therapeutic beam incident from the light-incident part to an eyeball; a first sensing part arranged between the light-incident part and the light-emitting part so as to sense the reaction occurring in a healing site of the eyeball on which the therapeutic beam is irradiated; and a second sensing part arranged in a region of the light-emitting part spaced from the first sensing part so as to sense whether contact has been made with the eyeball.

9 Claims, 12 Drawing Sheets

CONTACT LENS AND OPHTHALMIC TREATMENT DEVICE HAVING SAME

RELATED APPLICATIONS:

This Application is a 35 U.S.C. § 371 National Stage filing of International Application No. PCT/KR2014/006590, filed on Jul. 21, 2014, which claims benefit of and priority to Korean Patent Application No. 10-2013-0087976, filed on Jul. 25, 2013. The contents of each of the above applications are hereby incorporated by reference in their entirety.

BACKGROUND OF THE INVENTION

Field of the Invention

The present invention relates to a contact lens and an ophthalmic device having the same and, more particularly, to a contact lens for viewing the retina, etc. of an eye or for generating a treatment beam and guiding it to the eye and an ophthalmic device having the same.

Related Art

In general, contact lenses for use in ophthalmology are used when ophthalmologists are required to place them in contact with a patient's eye for eye examinations. Such contact lenses are used particularly for retinal examination. They are also used to deliver a treatment beam to the eye for ophthalmic therapy purposes. These contact lenses are used together with ophthalmic devices for generating a treatment beam and delivering it to the eye.

More concretely, a contact lens serves to adjust the path of a treatment beam from an ophthalmic device. For an eye examination or treatment, the ophthalmologist has to bring the contact lens into contact with the patient's eye by holding it with hand.

A conventional contact lens and an ophthalmic device having the same are disclosed in U.S. Pat. No. 6,698,886 titled "Iridotomy and trabeculoplasty goniolaser lens". When using the contact lens disclosed in the related-art document "Iridotomy and trabeculoplasty goniolaser lens", the ophthalmologist has to rely on their senses or experience in order to tell whether the contact lens is placed in contact with the eye before delivering a treatment beam. They also have to manually adjust the position of the contact lens to place it in contact with the eye to be checked or treated.

Since the contact lens disclosed in the related-art document requires the ophthalmologist to tell by their own senses or experience how it is being brought into contact with the eye, they cannot make sure whether it is correctly placed in contact with the eye and this may lead to errors in the delivery of a treatment beam. Moreover, the ophthalmologist will feel more fatigue because they have to bring the contact lens into contact with the patient's eye by holding it with fingers.

SUMMARY OF THE INVENTION

The present invention provides a contact lens that is improved in structure so as to allow an ophthalmologist to make sure whether it is placed in contact with a patient's eye and an ophthalmic device having the same.

In addition, the present invention provides a contact lens that is improved in structure so as to automatically adjust the position of the contact lens to get it placed in contact with the patient's eye and an ophthalmic device having the same.

According to an exemplary embodiment of the present invention, a contact lens for guiding a treatment beam directed from a beam generator to the eye may include: a housing including an entrance part through which the treatment beam directed from the beam generator enters and an exit part through which the treatment beam entering through the entrance part is guided to the eye; a first detecting part located between the entrance part and the exit part and detecting a reaction in a treated area of the eye to which the treatment beam is delivered; and a second detecting part located in the area of the exit part, spaced apart from the first detecting part, and detecting whether there is contact with the eye.

According to another exemplary embodiment of the present invention, a contact lens for guiding a treatment beam directed from a beam generator to the eye may include: a first housing including an entrance part through which the treatment beam directed from the beam generator enters; a second housing detachably attached to an opening area opposite the entrance part of the first housing and including an exit part through which the treatment beam entering through the entrance part exits; a first detecting part located in either the first housing or the second housing and detecting a reaction in a treated area of the eye to which the treatment beam is delivered; and a second detecting part located in the area of the exit part and detecting whether there is contact between the second housing and the eye.

Preferably, the first detecting part may be located inside the second housing, spaced apart from the second detecting part.

Preferably, the first detecting part may detect the amount of bubbles in the treated area of the eye, generated by the delivery of the treatment beam.

Preferably, the operation of the beam generator may be controlled in response to a detection signal from the second detecting part.

Any one of the first and second housings may include hooks, and the other housing may include hook joints that engage with the hooks to detachably hold the first housing and the second housing together.

Preferably, the first housing and the second housing may be held together by either screwing or pinning.

The first detecting part and the second detecting part may include an ultrasonic sensor and a proximity sensor, respectively.

The contact lens may further include a gaze part that is located in an inner region visible to the eye and that prevent the patient's eye from moving by emitting gaze fixation light to forms a point of gaze.

According to yet another exemplary embodiment of the present invention, an ophthalmic device that delivers a treatment beam directed from a beam generator to the eye may include: a main body accommodating the beam generator; a contact lens that is brought close to the eye and guides the treatment beam directed from the beam generator to the eye, the contact lens including a first housing including an entrance part through which the treatment beam directed from the beam generator enters, a second housing detachably attached to an opening area opposite the entrance part of the first housing and including an exit part through which the treatment beam entering through the entrance part exits, a first detecting part located in either the first housing or the second housing and detecting a reaction in a treated area of the eye to which the treatment beam is delivered, and a second detecting part located in the area of the exit part and detecting whether there is contact between the second housing and the eye; a holder unit detachably attached to the contact lens and rotating the contact lens relative to the eye;

and a connecting unit located between the main body and the holder unit and connecting the main body and the holder unit together.

The holder unit may include: a rotation support unit that supports the contact lens and that rotates the contact lens about at least one axis such as an X-axis on which the contact lens pivots, a Y-axis on which the contact lens tilts, or a Z-axis on which the contact lens swivels; and a driving unit that is connected to the rotation support unit and that provides a driving force to cause the rotation support unit to either pivot, tilt, or swivel.

Preferably, the rotation support unit may be detachably attached to the first housing of the contact lens.

Preferably, the first housing of the contact lens and the rotation support unit may be detachably held together by either pinning, hooking, or fitting.

The connecting unit may include: a first connector that is connected to the main body and that reciprocates along the Y-axis on which the holder support tilts; and a second connector that connects the first connector and the holder unit together in a direction transverse to the movement direction of the first connector and that reciprocates along the Z-axis on which the holder support swivels.

The ophthalmic device may further include: an input part that applies an actuation signal to the holder unit and the connecting unit; and a control unit including a first controller for controlling the operation of the holder unit and of the connecting unit based on the actuation signal from the input part and a second controller for controlling the operation of the beam generator based on signals from the first detecting part and second detecting part.

Preferably, if the contact lens is deemed to be in contact with the eye, based on a detection signal from the second detecting part, the second controller may control the operation of the beam generator such that the treatment beam is delivered to the eye.

More preferably, the first detecting part may detect the amount of bubbles in the treated area of the eye, generated by the delivery of the treatment beam.

A hook located in any one of the first and second housings comprise hook and a hook joint located in the other housing and engaging with the hook to detachably hold the first housing and second housing together are provided.

The first housing and the second housing may be held together by either screwing or pinning.

The contact lens may further include a gaze part that is located in an inner region visible to the eye and that prevent the patient's eye from moving by emitting gaze fixation light to forms a point of gaze.

Other specific details of the embodiments are included in the detailed description and the accompanying drawings.

A contact lens and an ophthalmic device having the same have the following advantageous effects.

First, the second detecting part capable of detecting whether the contact lens is placed in contact with the eye and the first detecting part capable of detecting a change in the status of the eye caused by the delivery of a treatment beam may be provided inside the contact lens, thus improving the reliability of the product.

Second, the contact lens includes a housing that accommodates the first and second detecting parts and a housing that can be held by the operator, and these housings may be detachably held together. Accordingly, the housings may be replaced individually if the first detecting part or the second detecting part breaks down, thus reducing repair and maintenance costs of this product.

Third, the detachable contact lens may be adjusted to the accurate contact position with respect to the patience's eye since it can be automatically adjusted to allow the contact lens to pivot, tilt, or swivel and to move horizontally and vertically. This allows for more accurate treatment and reduces the operator's fatigue.

DESCRIPTION OF EXEMPLARY EMBODIMENTS

Hereinafter, a contact lens and an ophthalmic device having the same according to an embodiment of the present invention will be described in detail with reference to the accompanying drawings.

Prior to describing the invention, it is to be noted beforehand that different reference numerals are used to designate identical elements between contact lenses according to first and second embodiments of the present invention. Also, it should be noted beforehand that a contact lens according to a third embodiment further includes a gaze part, in addition to the elements of the contact lens according to the second embodiment, and the same elements as the second embodiment are denoted by the same reference numerals as the second embodiment.

An ophthalmic device according to an embodiment of the present invention is described as including the contact lens according to the third embodiment of the present invention.

Figure 1:
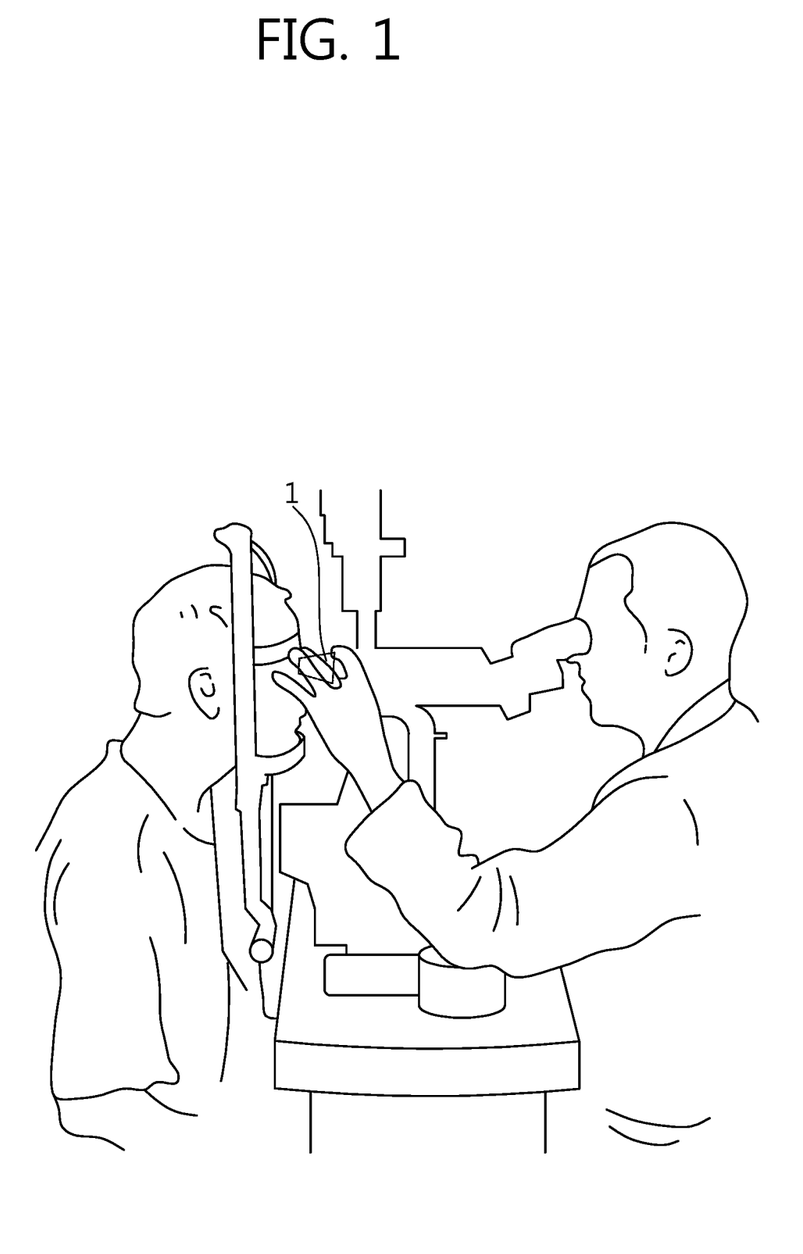
FIG. 1 illustrates a contact lens being placed in contact with a patient's eye according to embodiments of the present invention.
Figure 2:
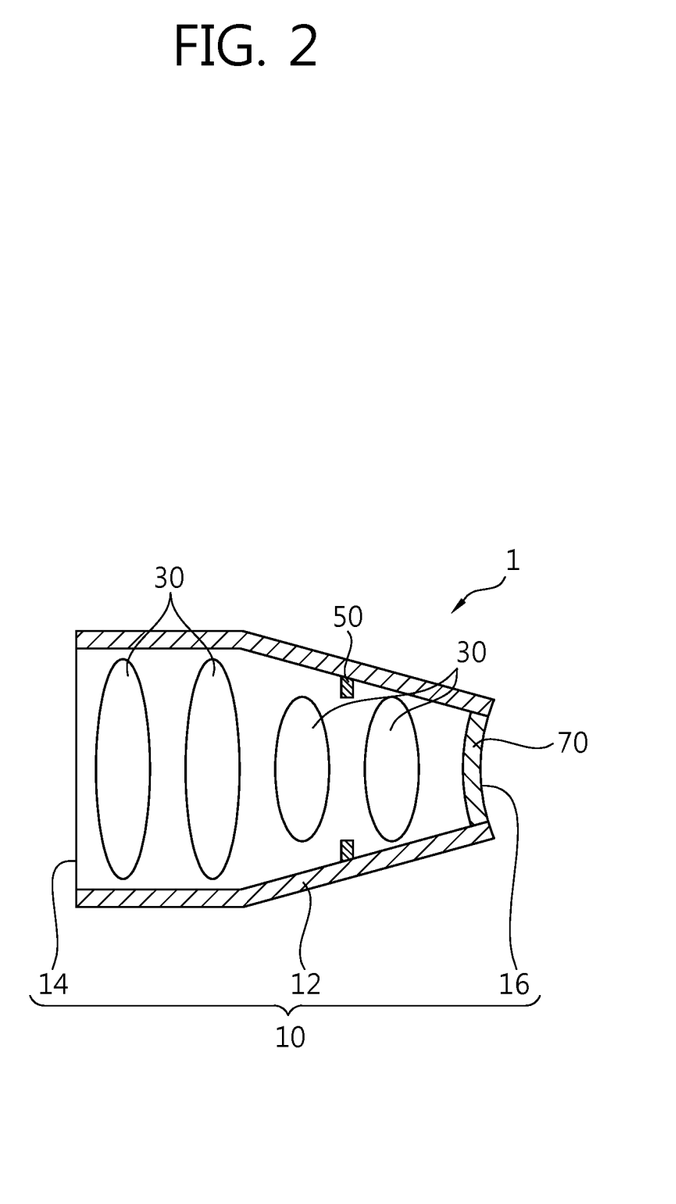
FIG. 2 is a cross-sectional view of a contact lens according to a first embodiment of the present invention.

FIG. 1 illustrates a contact lens being placed in contact with a patient's eye according to embodiments of the present invention. FIG. 2 is a cross-sectional view of a contact lens according to a first embodiment of the present invention.

As illustrated in FIGS. 1 and 2, a contact lens 1 according to the first embodiment of the present invention includes a housing 10, a lens part 30, a first detecting part 50, and a second detecting part 70.

The housing 10 includes a main body 10, an entrance part 14, and an exit part 16. The main body 12 of the housing 10 accommodates the lens part 30, the first detecting part 50, and the second detecting part 70. Also, the main body 12 of the housing 10 forms the entrance part 14 and exit part 16 through which a treatment beam enters and exits. The exit part 16 is placed in contact with a patient's eye.

The lens part 30 is accommodated in the main body 12 of the housing 10 and guides a treatment beam entering through the entrance part 14 to the exit part 16. The lens part 30 consists of a plurality of concave lenses or convex lenses, and serves to collimate the treatment beam entering through the entrance part 14 or change the exit path of the treatment beam.

The first detecting part 50 is located between the entrance part 14 and the exit part 16, inside the main body 12 of the housing 10. The first detecting part 50 detects a reaction in a treated area of the eye to which a treatment beam is delivered. That is, the first detecting part 50 detects the amount of bubbles generated when a treatment beam is delivered to the eye. In one embodiment of the present invention, an ultrasonic sensor is used as the first detecting part 50. Alternatively, various well-known sensors capable of detecting the amount of bubbles in the eye, generated by the delivery of a treatment beam, as well as the ultrasonic sensor, may be used as the first detecting part 50.

The second detecting part 70 is located in the area of the exit part 16 of the housing 10, spaced apart from the first detecting part 50. The second detecting part 70 detects whether there is contact with the eye. In one embodiment of the present invention, a proximity sensor is used as the second detecting part 70. The ophthalmologist can tell whether the contact lens 1 is placed in contact with the eye, based on a detection signal from the second detecting part 70.

Figure 3:
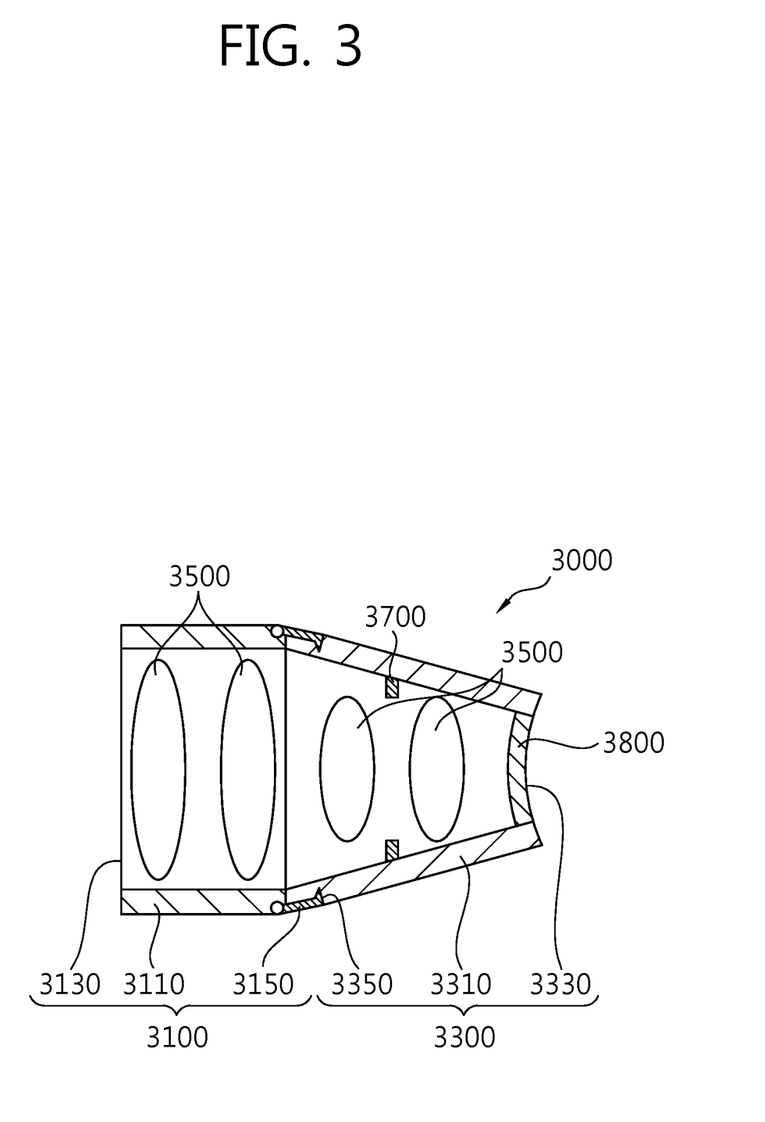
FIG. 3 is a cross-sectional view of a contact lens according to a second embodiment of the present invention.

FIG. 3 is a cross-sectional view of a contact lens according to the second embodiment of the present invention.

As illustrated in FIG. 3, a contact lens 3000 according to the second embodiment of the present invention includes a first housing 3100, a second housing 3300, a lens part 3500, a first detecting part 3700, and a second detecting part 3800. Unlike the contact lens 1 according to the first embodiment of the present invention, the first and second housings 3100 and 3300 of the contact lens 3000 according to the second embodiment of the present invention are detachably held together.

The first detecting part 3700 is located in either the first housing 3100 or the second housing 3300 and detects a reaction in a treated area of the eye to which a treatment beam is delivered. Preferably, the first detecting part 3700 and the second detecting part 3800 may be located together inside the second housing 3300, as in the first embodiment of the present invention.

The second detecting part 3800 is located inside the second housing 3300 and detects whether there is contact with the eye. A proximity sensor is used as the second detecting part 3800.

As such, the contact lens 3300 according to the second embodiment of the present invention has the advantage that the first housing 3100 and the second housing 3300 may be replaced individually if the first detecting part 3700 or the second detecting part 3800 breaks down, since the first housing 3100 and the second housing 3300 are detachably held together. Therefore, repair and maintenance costs of this product may be reduced.

Figure 4:
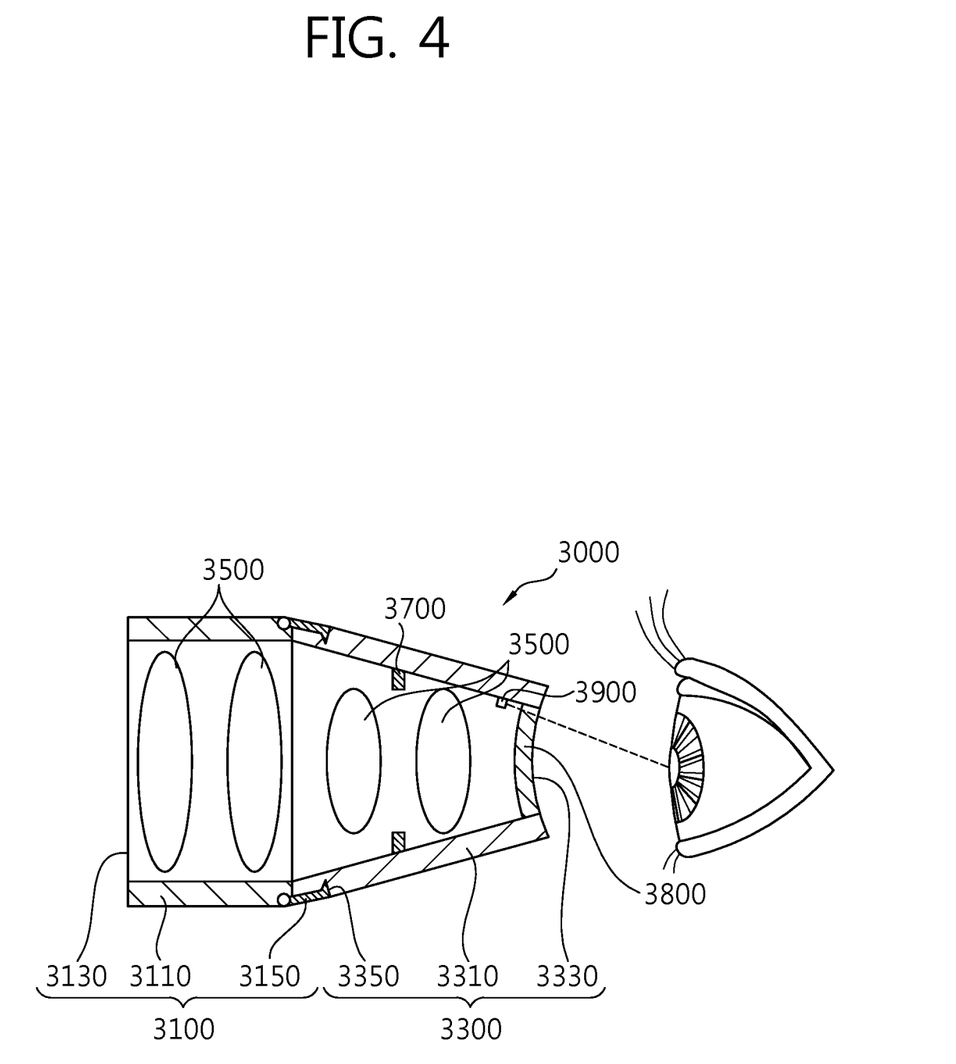
FIG. 4 is a cross-sectional view of a contact lens according to a third embodiment of the present invention.

FIG. 4 is a cross-sectional view of a contact lens according to the third embodiment of the present invention.

As illustrated in FIG. 4, a contact lens 300 according to the third embodiment of the present invention includes a first housing 3100, a second housing 3300, a lens part 3500, a first detecting part 3700, a second detecting part 3800, and a gaze part 3900. That is, the contact lens 300 according to the third embodiment of the present invention further includes a gaze part 3900, in addition to the contact lens 3000 according to the second embodiment.

The gaze part 3900 is located in an inner region visible to the eye and emits gaze fixation light for the patient to look at that forms a point of gaze. The gaze part 3900 is prepared as a light source that is located inside the contact lens 3000, close to the eye and that emits light for the patient to look at that is visible to the eye. In particular, the gaze part 3900 emits a wide wavelength band of light for the patient to look at to form a point of gaze visible to the eye. The light for the patient to look at that is emitted by the gaze part 3900 forms a point of gaze at which the eye is looking, thereby preventing the eye from moving when the contact lens 3000 is in contact with the eye.

The gaze part 3900 is applicable to the contact lens 1 of the first embodiment of the present invention, as well as to the contact lens 3000 of the second embodiment of the present invention.

Figure 5:
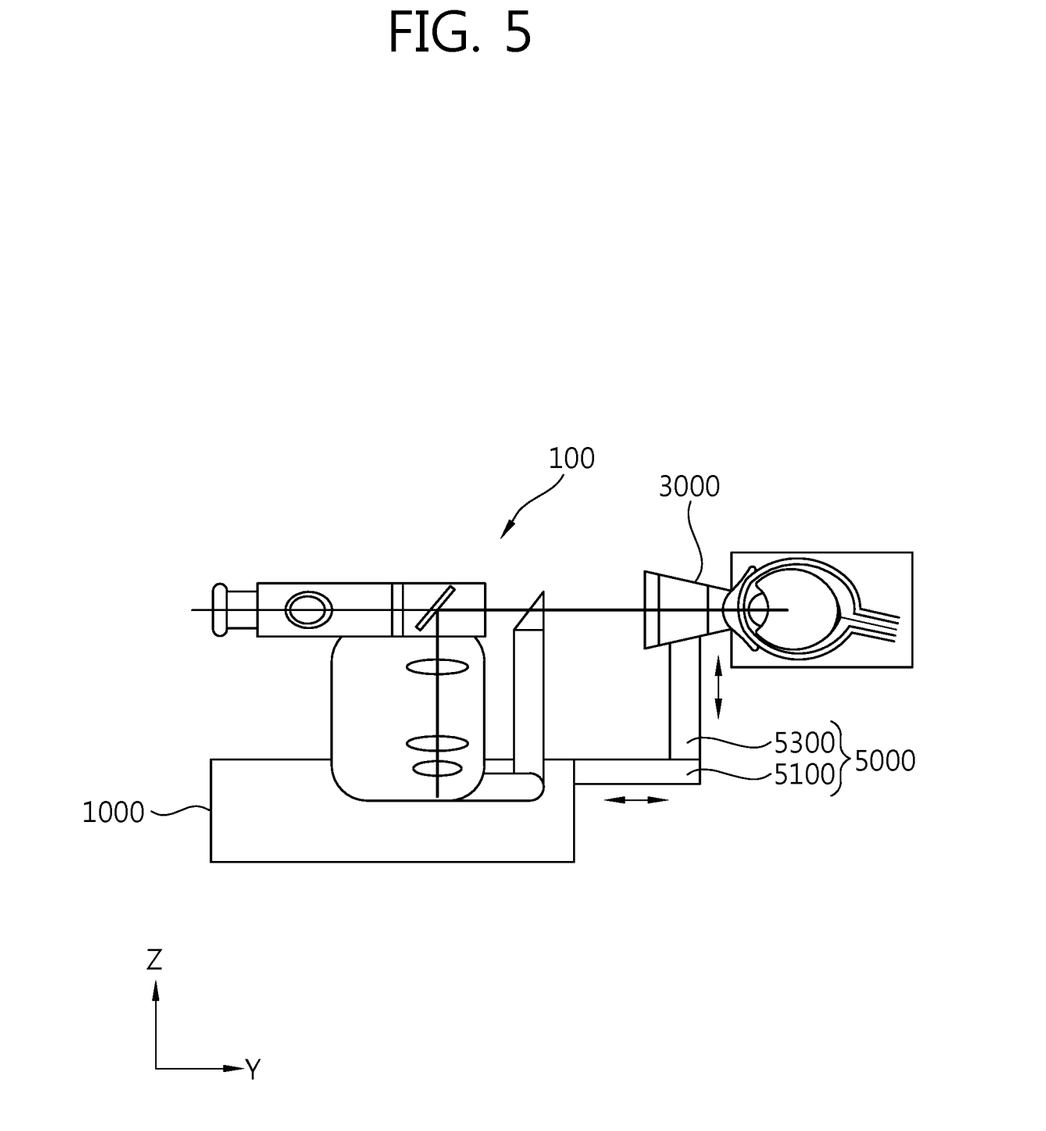
FIG. 5 is a schematic diagram of an ophthalmic device including the contact lens of FIG. 4 according to an embodiment of the present invention.
Figure 6:
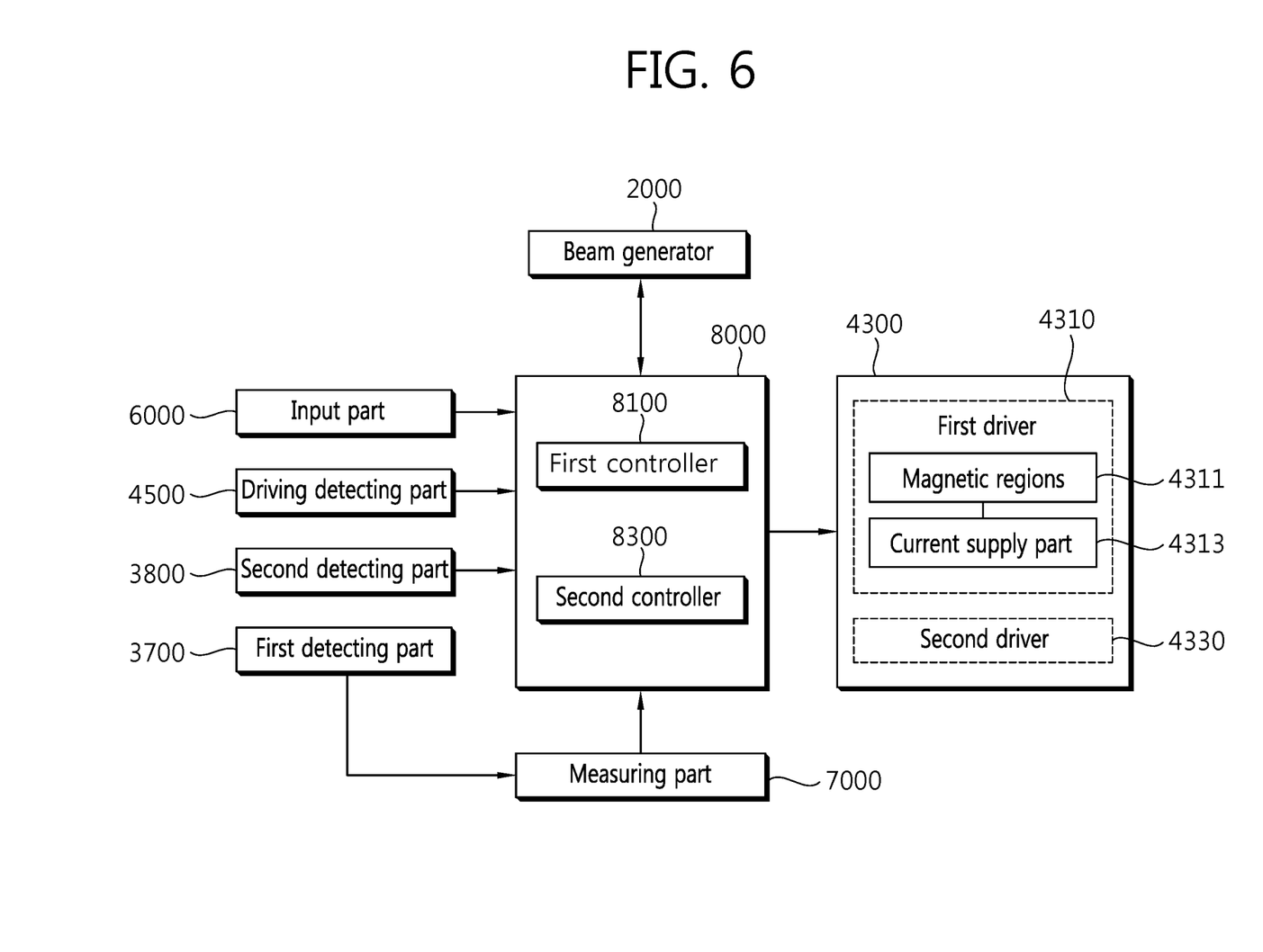
FIG. 6 is a control block diagram of an ophthalmic device according to the present invention.
Figure 7:
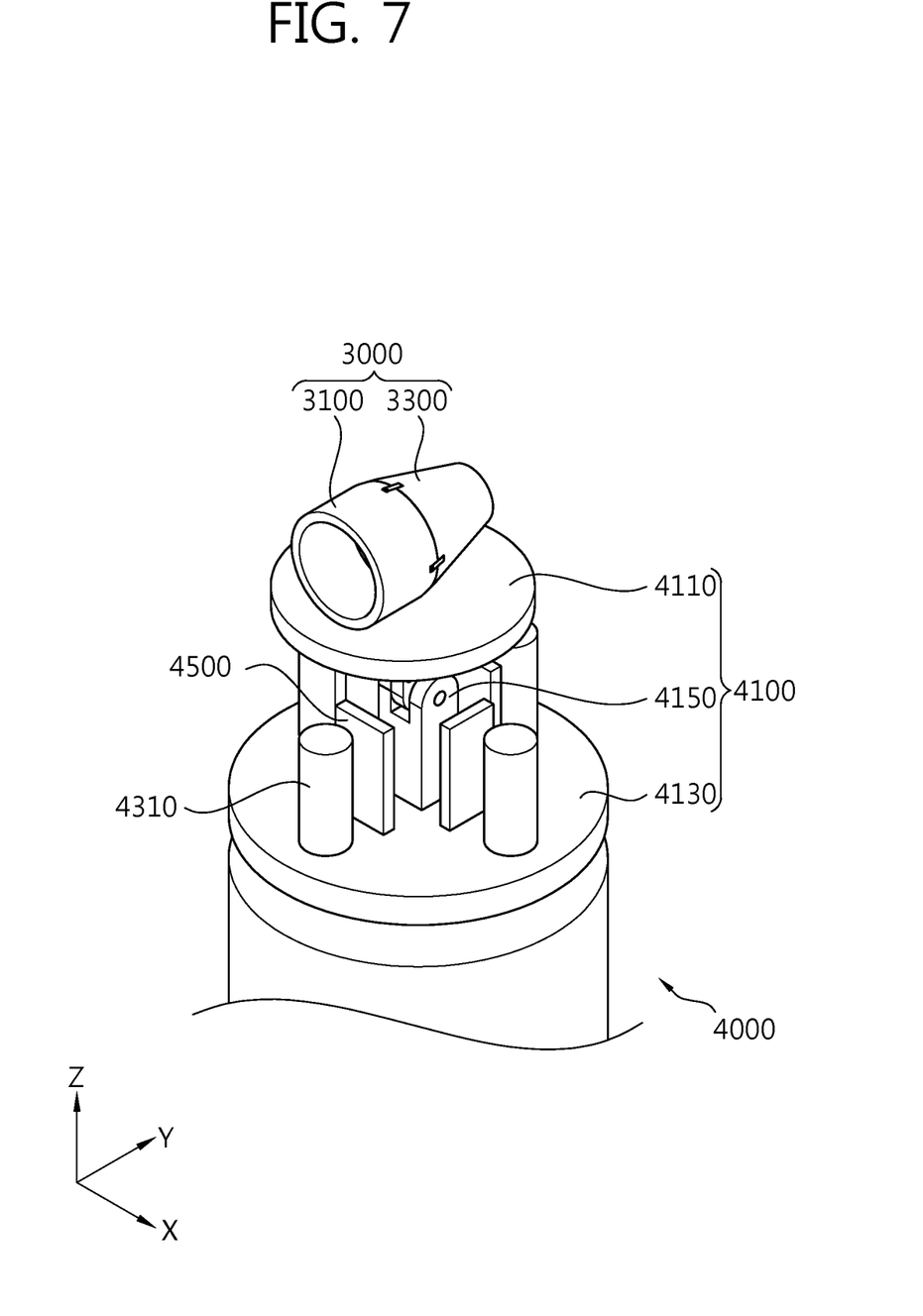
FIG. 7 is a combined perspective view of a contact lens and a rotation support unit according to the present invention.
Figure 8:
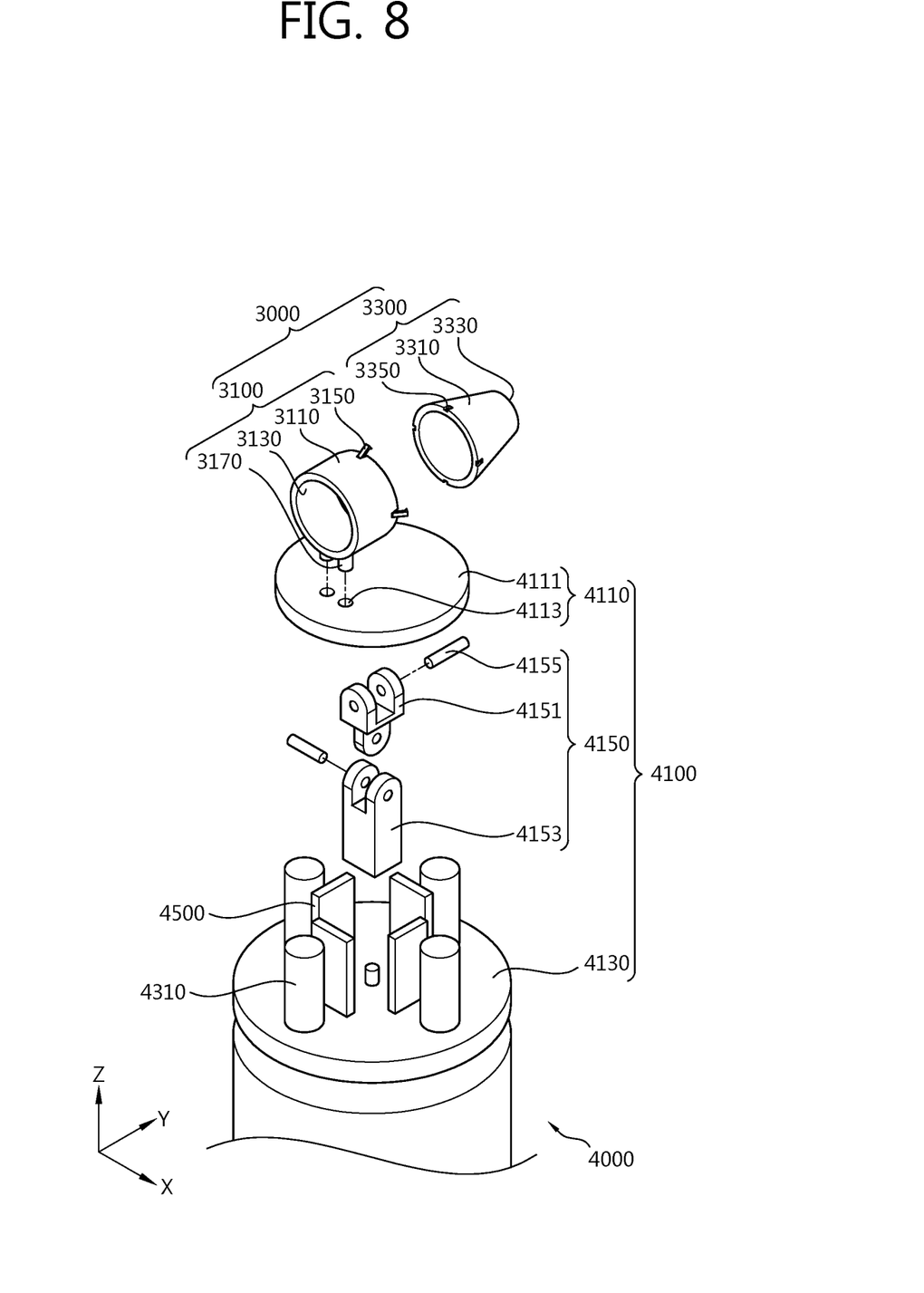
FIG. 8 is an exploded perspective view of a contact lens and a rotation support unit according to the present invention.

FIG. 5 is a schematic diagram of an ophthalmic device including the contact lens of FIG. 4 according to an embodiment of the present invention. FIG. 6 is a control block diagram of an ophthalmic device according to the present invention. FIG. 7 is a combined perspective view of a contact lens and a rotation support unit according to the present invention. FIG. 8 is an exploded perspective view of a contact lens and a rotation support unit according to the present invention.

As illustrated in FIGS. 5 to 8, an ophthalmic device 100 including the contact lens 3000 according to the third embodiment of the present invention includes a main body 1000, a beam generator 2000, the contact lens 3000, a holder unit 4000, a connecting unit 5000, an input part 6000, a measuring part 7000, and a control unit 8000.

The main body 1000 constitutes the outer appearance of the ophthalmic device 100, and includes an eye examination part (not shown) such as a microscope that can magnify, with which the patient's eye can be examined.

The beam generator 2000 is equipped within the main body 1000 and generates a treatment beam and emits it to the contact lens 3000. The beam generator 2000 includes a laser diode in order to generate and emit laser light used as a treatment beam. For example, a Q-switched Nd:YAG laser, etc. may be used as the beam generator 2000.

The contact lens 3000 includes a first housing 3100, a second housing 3300, a lens part 3500, a first detecting part 3700, a second detecting part 3800, and a gaze part 3900. The first and second housings 3100 and 3300 of the contact lens 3000 are detachably held together. The first housing 3100 is held in the holder unit 4000, and the second housing 3300 is detachably attached to the first housing 3100 held in the holder unit 4000.

The first housing 3100 includes a first housing body 3110, an entrance part 3130, hooks 3150, and connecting pins 3170. The first housing body 3110 forms the outer appearance of the first housing 3100, and one side of the first housing body 3110 forms the entrance part 3130 through which a treatment beam generated from the beam generator 3000 enters.

The hooks 3150 are provided to detachably hold the first housing 3100 and the second housing 3300 together. While the hooks 3150 are provided on the first housing 3110 in one embodiment of the present invention, they may be switched with hook joints 3350 of the second housing 3300 to be described later and provided on the second housing 3300. Using the hooks 3150 is an example of the method of detachably holding the first housing body 3110 and a second housing body 3310 together, and various well-known joining methods such as pinning or screwing may be used instead of using the hooks 3150.

The connecting pins 3170 is located downward from the first housing body 3110. The connecting pins 3170 are attached to the holder unit 4000. More specifically, the connecting pins 3170 are attached to pin joints 4113 of a holder support 4110 to be described later to hold the holder unit 4000 and the first housing 3100 of the contact lens 3000 together. Needless to say, the connecting pins 3170 are merely an example, and the holder unit 4000 and the first housing 3100 of the contact lens 3000 may be held together by various well-known joining methods such as hooking or screwing.

The second housing 3300 includes the second housing body 3310, an exit part 3330, and the hook joints 3350. The second housing body 3310 guides a treatment beam entering through the entrance part 3130 of the first housing 3100 to the patient's eye. In this instance, the exit part 3330 needs to be placed in contact with the patient's eye. The hook joints 3350 are provided on the second housing 3310 in one embodiment of the present invention. More specifically, the hook joints 3350 are provided at points where the first housing body 3110 and the second housing body 3310 are held together. As described above, the hook joints 3350 may be switched with the hooks 3150 of the first housing 3100, rather than being provided on the second housing body 3310. For example, if the hooks 3150 of the first housing 3100 are located on the second housing 3300, the hook joints 3350 of the second housing 3300 are provided on the first housing 3100.

The lens part 3500 is accommodated in the first housing body 3110 and the second housing body 3310. The lens part 3500 is a combination of convex lenses and concave lenses, and serves to collimate a treatment beam entering through the entrance part 3130 or regulate the exit path of the treatment beam and guide it to the exit part 3330.

The first detecting part 3700 and the second detecting part 3800 are accommodated in the second housing body 3310 in one embodiment of the present invention. An ultrasonic sensor and a proximity sensor are used as the first detecting part 3700 and the second detecting part 3800, respectively. The first detecting part 3700 is accommodated in the second housing body 3310, spaced apart from the second detecting part 3700. The first detecting part 3700 detects a reaction in the treated area of the eye and sends a detection signal to the control unit 8000. More specifically, the first detecting part 3700 detects the amount of bubbles in the treated area of the eye, generated by the delivery of a treatment beam and sends a detection signal to the control unit 8000. Based on the detection signal from the first detecting part 3700, the control unit 8000 may control the operation of the beam generator 3000 or of a beam delivery part that is not shown in the present disclosure.

The second detecting part 3800 is located in the area of the exit part 3330 of the second housing 3300. The second detecting part 3800 detects whether the contact lens 3000 is placed in contact with the patient's eye. A detection signal from the second detecting part 3800 is sent to the control unit 8000. Based on the signal from the second detecting part 3800, the operation of the beam generator 2000 or of the beam delivery part is controlled. For example, if the contact lens 3000 is deemed to be in contact with the eye, based on the signal from the second detecting part 3800, a second controller 8300 of the control unit 8000 to be described later controls the operation of the beam generator 2000 so as to deliver a treatment beam to the treated area of the eye.

Figure 9:
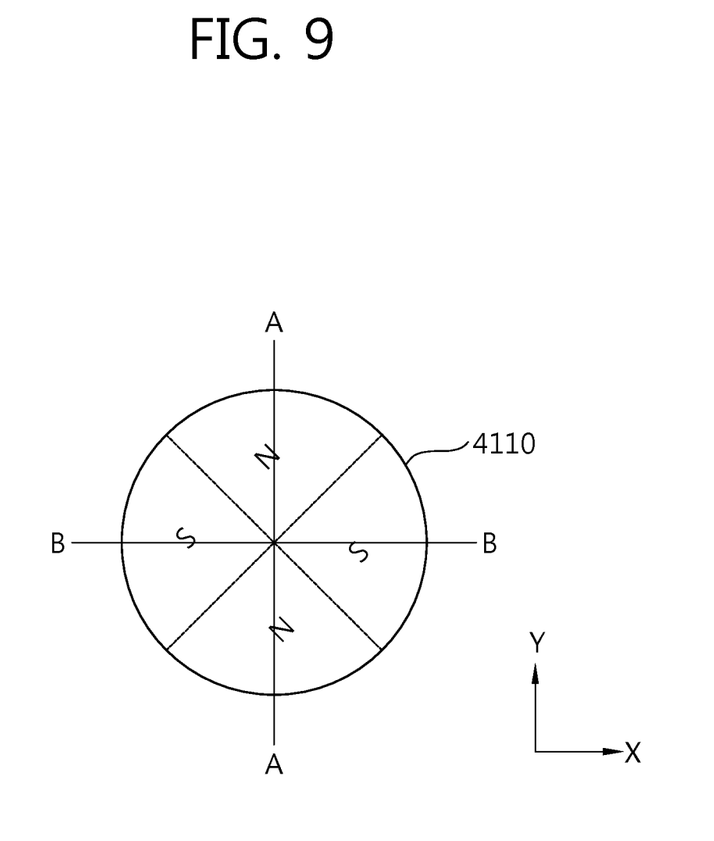
FIG. 9 is a view of a first magnetic polarity of the holder support of the rotation support unit of FIG. 8.
Figure 10:
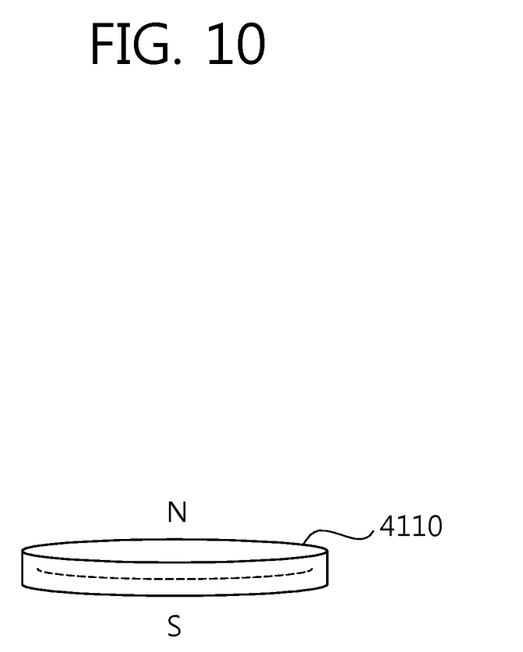
FIG. 10 is a view of a second magnetic polarity of the holder support of the rotation support unit of FIG. 8.
Figure 11:
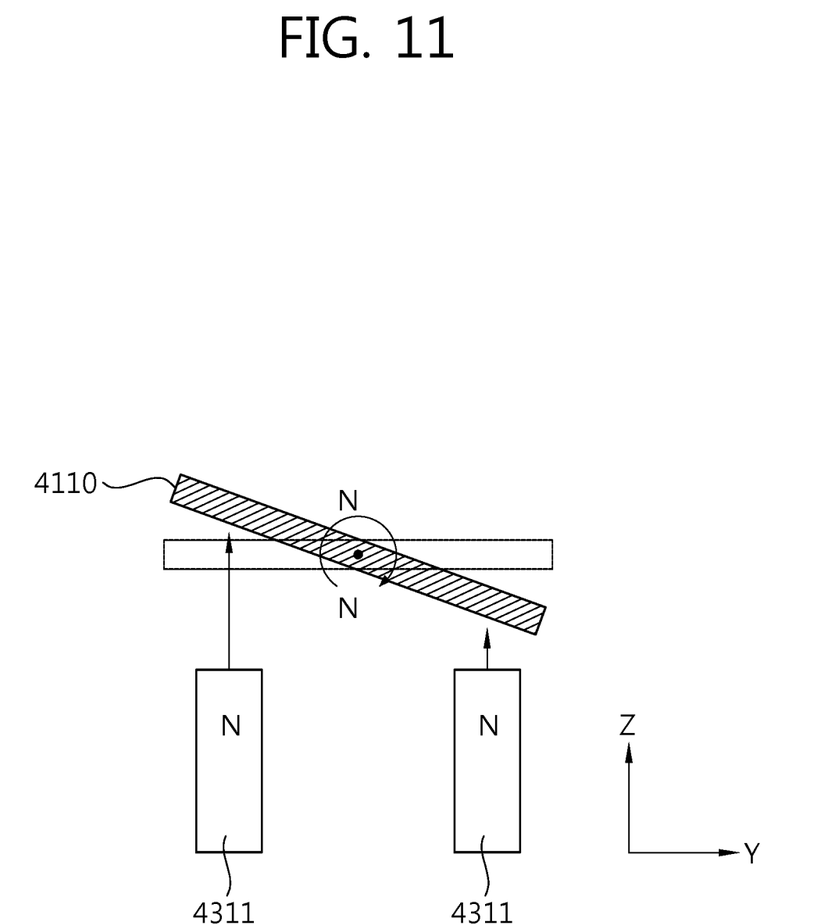
FIG. 11 is an operational view of how the rotation support unit is actuated by the magnetic polarity indicated by the line A-A of FIG. 9.
Figure 12:
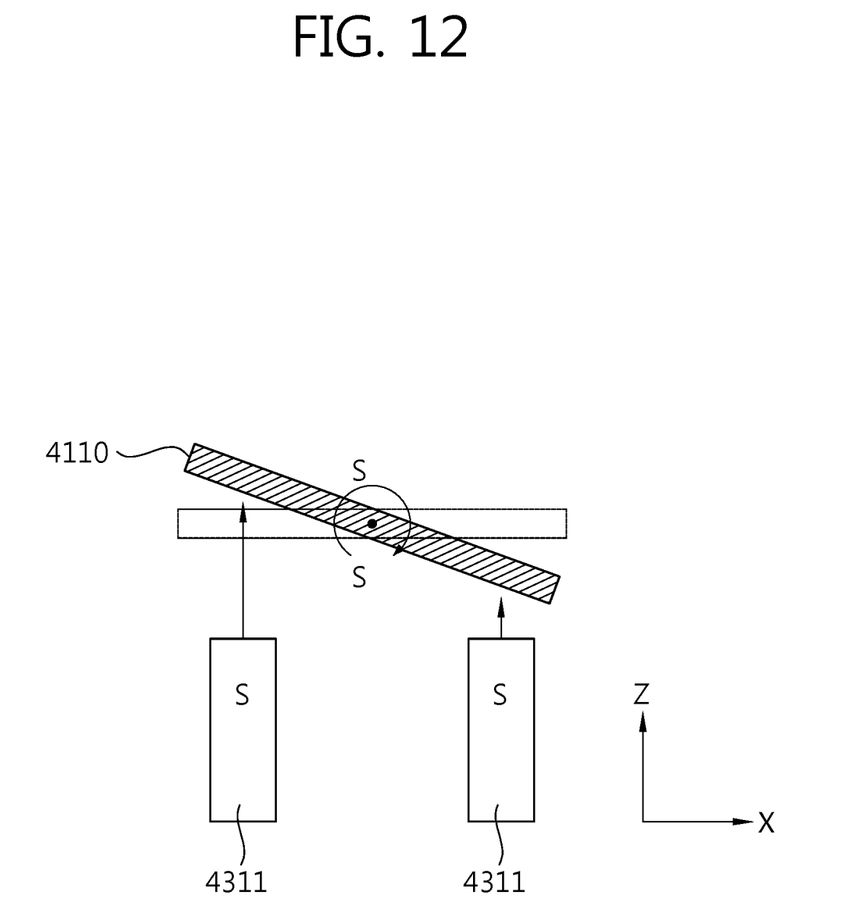
FIG. 12 is an operational view of how the rotation support unit is actuated by the magnetic polarity indicated by the line B-B of FIG. 9.

FIG. 9 is a view of a first magnetic polarity of the holder support of the rotation support unit of FIG. 8. FIG. 10 is a view of a second magnetic polarity of the holder support of the rotation support unit of FIG. 8. FIG. 11 is an operational view of how the rotation support unit is actuated by the magnetic polarity indicated by the line A-A of FIG. 9. FIG. 12 is an operational view of how the rotation support unit is actuated by the magnetic polarity indicated by the line B-B of FIG. 9.

The holder unit 4000 is detachably attached to the contact lens 3000, and rotates the contact lens 3000 relative to the eye. That is, the holder unit 4000 operates in a way that automatically adjusts the position of the contact lens 3000 in response to an input signal from the operator. In one embodiment of the present invention, the holder unit 4000 includes a rotation support unit 4100, a driving unit 4300, and a driving detecting part 4500.

The rotation support unit 4100 includes a holder support 4110, a rotation stage 4130, and a rotary joint part 4150. The rotation support unit 4100 supports the contact lens 3000, and rotates the contact lens 3000 about at least one axis such as an X-axis on which the contact lens 3000 pivots, a Y-axis on which the contact lens 3000 tilts, or a Z-axis on which the contact lens 3300 swivels. The pivoting, tilting, and swiveling of the rotation support unit 4100 are caused by a driving force from the driving unit 4300.

The holder support 4110 includes a support body 4111 and the pin joints 4113. The holder support 4110 detachably supports the contact lens 3000. The holder support 4110, in response to the operation of the rotation stage 4130 and of the rotary joint part 4150, causes the contact lens 3000 to pivot, tilt, and swivel.

The support body 4111 is formed in the shape of a magnetic disk. The support body 4111 is made from a magnetic material having an N pole and an S pole so that a magnetic force is generated between the support body 4111 and magnetic regions 4311 of a first driver 4310 to be described later. As illustrated in FIG. 9, the support body 4111 is made of a magnet that is split into four sections about the Z-axis, and each pair of two sections facing each other across the center point has the same pole. On the other hand, in another embodiment, the support body 4111 may be a magnet that is split into two horizontally, i.e., in the direction of the X-axis and has opposite N and S poles, as illustrated in FIG. 10. Regarding the operation of the support body 4111, the support body 4111 depicted in FIG. 9, together with the magnetic regions 4311 of the first driver 4310, will be described with reference to the operational views of FIGS. 11 and 12.

The pin joints 4113 are pierced through the surface of the support body 4111 on which the contact lens 3000 is supported. The pin joints 4113 and the connecting pins 3170 of the first housing 3100 are attached together. As such, the first housing 3100 of the contact lens 3000 is detachably attached to the holder support 4110. As the first housing 3100 is substantially detachably attached to the second housing 3300, it is deemed that the contact lens 3000 is detachably attached to the holder support 4110. The pin joints 4113 are merely an example of the present invention, and if hooks, etc. are used in place of the connecting pins 3170 of the first housing 3100 because of a design change, other types may substitute for the pin joints 4113.

The rotation stage 4130 is formed in a way that the holder support 4110 swivels. The rotation stage 4130 is connected to a second driver 4330 of the driving unit 4300 and rotates by the driving force of the second driver 4330. In this instance, the holder support 4110 and the rotation stage 4130 are connected together by the rotary joint part 4150, and the rotational force of the rotation stage 4130 is delivered to the holder support 4110 by the rotary joint part 4150.

The rotary joint part 4150 connects the holder support 4110 and the rotation stage 4130 together. In one embodiment of the present invention, the rotary joint part 4150 includes a first rotary joint part 4151, a second rotary joint part 4153, and a fastener member 4155. The rotary joint part 4150 is capable of receiving a rotational force from the rotation stage 4130 and transmitting a rotational driving force that swivels the holder support 4110. Also, a magnetic force generated between the support body 4111 of the holder support 4110 and the magnetic regions 4311 of the first driver 4310 make the rotary joint part 4150 pivot or tilt, thus pivoting or tilting the holder support 4110.

The first rotary joint part 4151 is rotatably attached to the bottom of the holder support 4110 and tilts the holder support 4110. The first rotary joint part 4151 does not substantially tilt the holder support 4110 in an active way, but instead guides the tilting of the holder support 4110 that rotates by a magnetic force between the S pole of the support body 4111 facing each other across the cross-section of the line B-B of FIG. 9 and the S pole of the magnetic regions of FIG. 12.

The second rotary joint part 4153 connects the first rotary joint part 4151 and the rotation stage 4130 together, and the second rotary joint part 4153 is attached to the first rotary joint part 4151 so that its axis of rotation (X-axis) is perpendicular to the axis of rotation of the first rotary joint part 4151. The second rotary joint part 4153 pivots the holder support 4110 by a driving force from the first driver 4310. The second rotary joint part 4153 does not substantially pivot the holder support 4110 in an active way, but instead guides the pivoting of the holder support 4110 that rotates by a magnetic force between the N pole of the support body 4111 facing each other across the cross-section of the line A-A of FIG. 9 and the N pole of the magnetic regions 4311 of FIG. 11.

The fastener member 4155 fastens the holder support 4110 and the first rotary joint part 4151 together so as to allow the holder support 4110 to tilt relative to the first rotary joint part 4151. Also, the fastener member 4155 fastens the first rotary joint part 4151 and the second rotary joint part 4153 so as to allow the holder support 4110 to pivot.

The driving unit 4300 includes the first driver 4310 and the second driver 4330. The first driver 4310 generates driving force to make the holder support 4110 pivot or tilt. The first driver 4310 includes the magnetic regions 4311 and a current supply part 4313.

The magnetic regions 4311 are having a pair of N pole and a pair of S pole, each pair facing each other along the X-axis and the Y-axis, respectively, and are placed at regular interval in a circumferential direction. The magnetic regions 4311 are located between the holder support 4110 and the rotation stage 4130, corresponding to the four sections of the holder support 4110 having an N pole and an S pole.

In one embodiment of the present invention, the magnetic regions 4311 form a magnetic force repulsive on the N pole or S pole of the holder support 4110, corresponding to the direction or amount of electric current from the current supply part 4313, thereby causing the holder support 4110 to pivot or tilt. Needless to say, the amount of electric current supplied from the current supply unit 4311 to the magnetic regions 4311 needs to be controlled so as to allow the holder support 4110 to pivot or tilt by adjusting the strength of the magnetic force of opposing magnetic regions. The magnetic regions 4311 of the holder support 4110 may be either permanent magnets or electromagnets.

The second driver 4330 transmits driving force to the rotation stage 4130. Preferably, a stepping motor may be used as the second driver 4330 to allow the holder support 4110 to swivel at a certain angle. Besides, various well-known driving mechanisms, such as motors, capable of finely adjusting the swivel angle or angular speed of the holder support 4110 may be used as the second driver 4330.

The driving detecting part 4500 is placed on the rotation stage 4130 and detects the adjusted position of the holder support 4110 relative to the operation of the holder support 4110. That is, the driving detecting part 4500 detects a changed position of the holder support 4110 caused by pivoting, tilting, or swiveling of the holder support 4110. The driving detecting part 4500 may be implemented as an optical sensor including a light source for emitting light and a light receiving part for detecting emitted light. The driving detecting part 4500, implemented as an optical sensor including the light source and the light receiving part, may detect the adjusted position of the holder support 4110 based on the amount of light received by the light receiving part.

Next, the connecting unit 5000 includes a first connecting unit 5000 and a second connecting unit 5000. The connecting unit 5000 connects the main body 1000 and the holder unit 4000 together. Also, the connecting unit 5000 reciprocates the holder unit 4000 along the Y-axis and the X-axis.

That is, the first connector 5100 of the connecting unit 5000 is connected to the main body 1000, and reciprocates along the Y-axis (horizontally) on which the holder support 4110 tilts. The second connector 5200 connects the first connector 5100 and the holder unit 4000 together in a direction transverse to the movement direction of the first connector 5100, and reciprocates along the Z-axis (vertically) on which the holder support 4110 swivels. The connecting unit 5000 may further include a connecting unit driver (not shown) that delivers driving force to the connecting unit 5000.

The input part 6000 is provided to apply an actuation signal to the holder unit 4000 and the connecting unit 5000. The input part 6000 may substantially apply an actuation signal to actuate the driving unit 4300 of the holder unit 4000 and an actuation signal to actuate the connecting unit 5000. Preferably, the input part 6000 may be located in an area the operator's hands can access easily.

The measuring part 7000 serves to measure a detection signal sent from the first detecting part 3700 of the contact lens 3000. For example, the measuring part 7000 measures a detection signal sent in real time from the first detecting part 3700, that is, information about the amount of bubbles generated in the treated area of the eye. In this way, the measuring part 7000 analyzes a signal sent in real time from the first detecting part 3700 and transmits it to the control unit 8000. For reference, although the measuring part 7000 is provided to analyze and measure a signal from the first detecting part 3700 in one embodiment of the present invention, the measuring part 7000 may be omitted so long as it has an algorithm by which a detection signal from the first detecting part 3700 is analyzed directly by the control unit 8000.

Lastly, the control unit 8000 may control the operation of the holder unit 4000 and of the connecting unit 5000 based on an actuation signal applied from the input part 6000, and also may control the operation of the beam generator 2000 or of the beam delivery part based on signals from the first detecting part 3700 and second detecting part 3800. In one embodiment of the present invention, the control unit 8000 includes a first controller 8100 and a second controller 8300.

The first controller 8100 controls the operation of the holder unit 4000 and of the connecting unit 5000 based on an actuation signal from the input part 6000. The second controller 8300 controls the operation of the beam generator 2000 based on signals from the first detecting part 3700 and second detecting part 3800. More specifically, as well as controlling the operation of the beam generator 2000 based on a signal from the measuring part 7000 that has measured a detection signal from the first detector 3700, the second controller 8300 of the present invention applies a control signal based on a detection signal from the second detecting part 3800 in such a way as to actuate the beam generator 2000 if the contact lens 3000 is in contact with the eye, or to stop the operation of the beam generator 2000 (or to keep the beam generator 2000 stopped) if the contact lens 3000 is not in contact with the eye.

With this construction in mind, the operational process of the ophthalmic device 100 according to the present invention will be described below. Prior to the description, it is to be noted that the operational process of the ophthalmic device 100 including the contact lens 3000 according to the third embodiment of the present invention will described.

First, the first housing 3100 and second housing 3300 of the contact lens 3000 are held together, and then the contact lens 3000 and the holder support 4110 are held together with the connecting pins 3170 of the first housing 3100 and the pin joints 4113 of the holder support 4110. Alternatively, the first housing 3100 may be attached to the holder support 4110 first, and then the second housing 3300 of the contact lens 3000 may be attached to the first housing 3100.

Next, the following first to fourth operational process steps are performed by applying an actuation signal to the input part 6000 so as to place the contact lens 3000 in contact with the patient's eye.

First, the connecting unit 5000 is actuated to bring the contact lens 3000 close to the eye Second, if pivoting of the contact lens 3000 is required, the current supply part 4313 of the first driver 4310 applies an electric current to the magnetic regions 4311 so as to generate a magnetic force between the holder support 4110 and the magnetic regions 4311.

Third, if tilting of the contact lens 3000 is required, the current supply part 4313 of the first driver 4310 applies an electric current to the magnetic regions 4311.

Fourth, if swiveling of the contact lens 3000 is required, the second driver 4330 is actuated to rotate the rotation stage 4130, thus causing the holder support 4110 to swivel.

Once the contact lens 3000 is placed in contact with the eye, the gaze part 3900 emits gaze fixation light for the patient to look at to prevent the eye from moving.

The above-mentioned first to fourth operational process steps are not sequentially performed, but may be performed selectively by the operator.

When the contact lens 3000 is brought close to the patient's eye by the operation of the holder unit 4000 and of the connecting unit 5000, the second detecting part 3800 generates a detection signal indicative of whether the contact lens 3000 is in contact with the eye. If the contact lens 3000 is deemed to be in contact with the eye, based on the detection signal from the second detecting part 3800, the second controller 8300 generates a control signal to actuate the beam generator 2000. The beam generator 2000 may be actuated automatically or by unlocking a device that applies an input signal to the beam generator 2000, in response to the control signal from the second controller 8300. On the contrary, if the contact lens 3000 is deemed to be not in contact with the eye, based on the detection signal from the second detecting part 3800, the second controller 8300 generates a control signal to not actuate the beam generator 2000.

During the delivery of a treatment beam to the treated area of the eye in response to a control signal from the second controller 8300, the first detecting part 3700 detects the amount of bubbles in the area to which the treatment beam is delivered. If it is deemed that a preset amount of bubbles is detected, based on a signal from the first detecting part 3700, the second controller 8300 generates a control signal to stop the operation of the beam generator 2000.

In view of this, the second detecting part capable of detecting whether the contact lens is placed in contact with the eye and the first detecting part capable of detecting a change in the status of the eye caused by the delivery of a treatment beam may be provided inside the contact lens, thus improving the reliability of the product.

Although the foregoing embodiments of the present invention have been described with reference to the attached drawings, it will be understood by those of ordinary skill in the art to which the present invention pertains that the present invention may be embodied in other specific forms without changing the technical idea or essential features of the present invention. Accordingly, it should be understood that the above-described embodiments are exemplary in all aspects and do not limit the scope of the present invention. The scope of the present invention is defined by the appended claims rather than the detailed description as described above, and it will be construed that all changes and modifications derived from the meanings and scope of the following claims and the equivalent concept fall within the scope of the present invention.

What is claimed is:

1. A contact lens for guiding a treatment beam directed from a beam generator to a retina of an eye, the contact lens comprising:

a housing including an entrance part through which the treatment beam directed from the beam generator enters and an exit part through which the treatment beam entering through the entrance part is guided to the eye;

a first detecting part located in the housing between the entrance part and the exit part and detecting a reaction in a treated area of the retina while the treatment beam is delivered to the treated area so as to control treatment beam radiation during the delivery of the treatment beam; and a second detecting part located in the area of the exit part, spaced apart from the first detecting part, and detecting whether there is contact with the eye.

2. A contact lens for guiding a treatment beam directed from a beam generator to a retina of an eye, the contact lens comprising:

a first housing including an entrance part through which the treatment beam directed from the beam generator enters;

a second housing detachably attached to an opening area opposite to the entrance part of the first housing and including an exit part through which the treatment beam entering through the entrance part exits;

a first detecting part located in either the first housing or the second housing and detecting a reaction in a treated area of the retina while the treatment beam is delivered to the treated area so as to control treatment beam radiation during the delivery of the treatment beam; and a second detecting part located in the area of the exit part and detecting whether there is contact between the second housing and the eye.

3. The contact lens of claim 2, wherein the first detecting part is located inside the second housing, spaced apart from the second detecting part.

4. The contact lens of claim 3, wherein the first detecting part detects an amount of bubbles in the treated area of the retina, generated by the delivery of the treatment beam.

5. The contact lens of claim 2, wherein the operation of the beam generator is controlled in response to a detection signal from the second detecting part.

6. The contact lens of claim 2, wherein one of the first or second housings comprises hooks, and the other housing comprises hook joints that engage with the hooks to detachably hold the first housing and the second housing together.

7. The contact lens of claim 2, wherein the first housing and the second housing are detachably held together by either screwing or pinning.

8. The contact lens of claim 2, wherein the first detecting part and the second detecting part comprises an ultrasonic sensor and a proximity sensor, respectively.

9. The contact lens of claim 2, further comprising a gaze part that is located in an inner region visible to the eye and that emits gaze fixation light for a patient to look at that forms a point of gaze to prevent the eye from moving.

* * * * *